United States Patent
Pillai et al.

(12) 
(10) Patent No.: US 6,548,072 B1
(45) Date of Patent: Apr. 15, 2003

(54) SKIN CARE COMPOSITIONS CONTAINING AN ORGANIC EXTRACT OF CHICK PEA

(75) Inventors: Sreekumar Pillai, Wayne, NJ (US); Uma Santhanam, Tenafly, NJ (US); Marieann Carlomusto, Palisades Park, NJ (US); Carol Annette Bosko, Oradell, NJ (US)

(73) Assignee: Chesebrough-Pond's USA Co., division of Conopco, Inc., Greenwich, CT (US)

( * ) Notice: Subject to any disclaimer, the term of this patent is extended or adjusted under 35 U.S.C. 154(b) by 781 days.

(21) Appl. No.: 09/398,898

(22) Filed: Sep. 20, 1999

Related U.S. Application Data

(63) Continuation of application No. 08/901,052, filed on Jul. 25, 1997, now Pat. No. 6,030,620.

(51) Int. Cl.[7] ............................ A61K 7/00; A61K 35/78
(52) U.S. Cl. ...................... 424/401; 424/757; 514/844; 514/874
(58) Field of Search ............................... 424/195.1, 401

(56) References Cited

U.S. PATENT DOCUMENTS

| | | | |
|---|---|---|---|
| 4,333,926 A | 6/1982 | Ohata et al. | 424/182 |
| 4,761,285 A | 8/1988 | Vasiliou et al. | 424/195.1 |
| 5,017,562 A | 5/1991 | Holmes et al. | 514/26 |

FOREIGN PATENT DOCUMENTS

| | | |
|---|---|---|
| FR | 2 759 295 | 8/1998 |
| WO | 93/23069 | * 11/1993 |
| WO | 96/38162 | 12/1996 |

OTHER PUBLICATIONS

Richards et al., "Human Dermal Fibroblasts Express Prolactin In Vitro", J. Invest. Dermatol., 106: 1250, 1996.
Creidi et al., "Effect Of A Conjugated Estrogen Cream On Aging Facial Skin", Maturitas, 19, p. 211, 1994.
Knight et al., "Phytoestrogens—A Short Review", Maturitas, 22: 167–75, 1995.
Price et al., "Naturally Occurring Estrogens in Foods—A Review", Food Additives and Contaminants., 2, p. 73–105 1985.
Girolomoni et al., "Prolactin Stimulates Proliferation of Cultured Human Keratinocytes", J. Invest. Dermatol 101: 275, 1993.
International Search Report in the application of PCT/EP 98/04224.
Derwent English language abstract of FR 2 759 295.
Dzeidzic et al., "Analysis of isoflavones in Bengalgram by high performance liquid chromatography", Journal of Chromatography, 234, 497–499, 1992.

* cited by examiner

*Primary Examiner*—Russell Travers
*Assistant Examiner*—Alysia Berman
(74) *Attorney, Agent, or Firm*—Ellen Plotkin

(57) ABSTRACT

Organic chick pea extracts are phytoestrogens, if present in an amount such as to provide an estrogenic activity equivalent to at least 1 nM of estradiol. Cosmetic compositions containing organic chick pea extracts are useful in improving the appearance of wrinkled, lined, dry, flaky, aged or photodamaged skin and improving skin thickness, elasticity, flexibility and plumpness.

1 Claim, No Drawings

SKIN CARE COMPOSITIONS CONTAINING AN ORGANIC EXTRACT OF CHICK PEA

This is a continuation of Ser. No. 08/901,052 filed Jul. 25, 1997, now U.S. Pat. No. 6,030,620.

FIELD OF THE INVENTION

Cosmetic compositions containing an organic extract of chick peas and methods of conditioning skin by applying such compositions to the skin.

BACKGROUND OF THE INVENTION

The human skin consists of two major layers, the bottom thicker layer dermis, and the top thinner layer—the epidermis. Dermis is the layer which provides the strength, elasticity and the thickness to the skin.

The main cell type of the dermis is fibroblasts, which is responsible for synthesis and secretion of all the dermal matrix components such as collagen, elastin and glycosaminoglycans. Collagen provides the strength, elastin the elasticity and glycosaminoglycans the moistness and plumpness of the skin. With aging, the thickness of the dermal layer is reduced and this is believed to be partially responsible for the formation of wrinkles in aging skin. The top layer of human skin or the epidermis which provides the resilience and the barrier properties of the skin, is composed of many different cell types including keratinocytes, melanocytes and langerhans cells. Keratinocytes are the major cell type of the epidermis (75–80% of the total number of cells in the human epidermis). Richards et al. reported that estrogen stimulates secretion of a protein, prolactin, by human dermal fibroblast cells and that prolactin then stimulates proliferation of keratinocytes. Richards et al., Human Dermal Fibroblasts Express Prolactin In Vitro., J. Invest. Dermatol., 106: 1250, 1996.

Estrogens and synthetic compounds which act like estrogens are known to increase the thickness of the dermal layer and reduce wrinkle formation in the aging skin. The changes in the skin such as skin dryness, loss of skin elasticity and plumpness occurring after menopause is attributed to the lack of estrogen production. Estrogen therapy prevents or slows down many of these changes associated with aging skin (Creidi et al., Effect of a conjugated estrogen cream on aging facial skin, Maturitas, 19, p. 211, 1994). Some of the effects of estrogen on skin include: increase in skin thickness and disappearance of fine wrinkles, increase of the mitotic rate of the epidermis, reduction in the size and activity of the sebaceous gland, slow down of the rate of hair growth, stimulation of collagen turnover and increase in the production of hyaluronic acid and glycosaminoglycan synthesis of the fibroblasts (Pugliese, Menopausal skin, Skin Inc., March/April 1994: p 69–77).

In recent years, phytoestrogens (i.e., natural compounds which have estrogen-like activity and which are found in plants) have been increasingly used for therapeutic purposes. Some of the uses described are as hypocholesterolemic and antiatherogenic agents, treatment of cardiovascular diseases especially in postmenopausal women, treatment for osteoporosis in the elderly and as an anticancer agent especially against breast cancer, endometrial and cervical cancer in women (Knight et al., Phytoestrogens—a short review, Maturitas, 22: 167–75, 1995).

The consumer demand for "natural" based products has been growing in recent years. The consumers perceive chemical synthesis as environmentally unsafe. A chemically synthesized ingredient may contain harsh chemicals. Natural products are perceived as pure and mild and superior to chemically synthesized products. However, delivering a cosmetic benefit from plant sources is not trivial. In order to derive a real benefit from a "natural" source not only a plant or a part of the plant containing a specific active has to be identified, but a minimum concentration and/or a specific extract of that plant has to be identified which truly delivers a cosmetic benefit.

Over 500 compounds present in plants have been described to have estrogenic activity. These compounds, collectively called phytoestrogens, are found in a diverse number of plants including cereals, legumes (including chick peas) and grasses (Price et al., Naturally occurring estrogens in foods- a review., Food additives and contaminants., 2, p. 73–106, 1985). Their concentrations vary in the different parts of the plants, geographical locations, year of growth etc. Two major classes of plant compounds which possess phytoestrogenic activity are flavonoids and coumestans. Some of the commonly described phytoestrogenic compounds are genistein, biochanin A, formononetin, daidzein and their glycoside derivatives (Knight et al., Phytoestrogens-a short review. Maturitas, J. Climactreic and post-menopause, 22, p.167–75, 1995).

Chick pea or Spanish pea (Cicer arietinum), a common dietary lentil, contains flavonoids including daidzein, formononetin, biochanin A, pratensein, homoferreirin, medicarpin, maackiain, methyl coumestrol, medicagol, formononetin glucoside and biochanin A glucoside (Ingham et al., In: Progress in the chemistry of Organic natural products, vol 43: Ed-W. Herz et al., Springer-Verlag, Wien, N.Y., 1983). The flavonoids from chick pea have been reported to have lipid lowering effects in the blood and liver of rats. Several nutritional studies report on the protein from chick pea for use as nutritional supplements and ways to improve the protein quality of chick pea. Vasiliou, U.S. Pat. No. 4,761,285 discloses the use of chick peas as a dietary supplement or for internal or topical treatment of hemorrhoids. In India, a cosmetic mask or skin treatment made from chick pea powder mixed with water is a common beauty treatment.

The art discussed above does not describe organic chick pea extracts for skin care or cosmetic use. The art does not teach topical application of organic chick pea extracts, as a phytoestrogen, and with a specified estrogenic activity.

SUMMARY OF THE INVENTION

The present invention includes a skin care composition comprising:
  (i) an organic extract of chick peas in an amount such as to provide an estrogenic activity equivalent to at least 1 nM of estradiol, the estrogenic activity being determined by the test described herein;
  (ii) a cosmetically acceptable vehicle.

The present invention also includes a method of improving or preventing the condition of wrinkled, lined, dry, flaky, aged or photodamaged skin and improving skin thickness, elasticity, flexibility and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to normal healthy skin to prevent or reduce the deteriorative changes.

The present invention also includes a cosmetic method of increasing fibroblast and epidermal skin cell proliferation in human skin by applying to the skin the inventive composition.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Chick Peas

Chick peas are suitable for use in the inventive compositions in the form of an organic extract. The chick pea extract is prepared for use in the present invention from dried chick peas. Dried chick peas may be obtained from Arrowhead Mills, from health food stores or supermarkets.

The organic chick pea extracts are prepared by extracting the. dried chick peas with a solvent by stirring 1 part of dried chick peas with 2 to 5 parts of the solvent for from 4 to 24 hours at room temperature. Suitable solvents are described hereinbelow. The extracts are clarified by filtration and/or centrifugation, then dried by evaporation (optionally, under vacuum) to obtain the organic chick pea extract.

Solvents suitable for: the preparation of chick pea extract for use herein include, but are not limited to: ethanol, methanol, hexane, chloroform, dichloromethane and ethyl acetate. The preferred solvents are dichloromethane, methanol, or ethanol in order to optimize activity. The extract may be further concentrated, fractioned, re-extracted or purified, e.g. by organic solvent extraction or by chromatography.

It has been found, as part of the present invention, that the organic chick pea extract has to be employed in a specific minimum amount to deliver an estrogenic activity.

Chick pea extract or powder is employed in an amount of from 0.0001 to 50%, as long as it delivers the estrogenic activity equivalent to at least 1 nM, generally in the range of from 1 nM to 100 nM, of estradiol. Estrogenic activity of the chick pea extract is determined by comparison to the activity of 1 nM estradiol using ZR-75 cells in a side by side experiment, as described in Example 1 below. Preferably, the chick pea extract is employed in an amount such as to deliver the estrogenic activity equivalent to at least 2 nM of estradiol.

Cosmetically Acceptable Vehicle

The composition according to the invention also comprises a cosmetically acceptable vehicle to act as a diluant, dispersant or carrier for the chick pea extract in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 $mm^2/s$ (centistokes) at 250° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid. esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical application to human skin, especially as an agent for conditioning, moisturizing and smoothening the skin, increasing its thickness, flexibility and elasticity and preventing or reducing the appearance of wrinkled, lined or aged skin.

In use, a small quantity of the composition, for example from 1 to 100 ml, is applied to exposed areas of the skin, from a suitable container or applicator and, if necessary, it is then. spread over and/or rubbed into the skin using the hand or fingers or a suitable device.

Product Form and Packagina

The topical skin care composition of the invention can be formulated as a lotion, a cream or a gel. The composition can be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The following specific examples further illustrate the invention, but the invention is not limited thereto. All p-values in the Examples were calculated using a student t-test.

EXAMPLE 1

This example illustrates that the organic chick pea extract at a concentration such as to provide a phytoestrogenic activity equivalent to at least 1 nM of estradiol is suitable for use in the present invention.

Preparation of Chick Pea Extracts:

Dried chick peas were obtained from Arrowhead Mills (Hareford, Tex.) and ground to a powder in a dry grinder. The chick pea powder thus obtained was extracted using dichloromethane (DCM) or methanol (1:3 w/v) by mixing the dry powder with the solvent for 20 hours at room temperature. The extracts were clarified by filtration and centrifugation. The extracts were then dried by evaporation under vacuum to obtain the dry extract. Extraction of 63 g of chick pea dry powder with DCM dissolved 1.47 g of dry material; extraction of 60 g of chick pea powder with methanol dissolved 2.434 g of dry material. This amounts to extraction of 2.31% by DCM and 4.06% by methanol. This dry extract was then redissolved in dimethyl sulfoxide (DMSO) at 50 μg/μl concentration for dosing the cells.

Methodology Used for Determining the Rate of DNA Synthesis in Cells:

The incorporation of $^3$H-thymidine by cultured cells was used as an assay of cell proliferation (ZR75 or keratinocyte). Thymidine is one of four deoxynucleosides which are the monomeric units of DNA. Prior to cell division of a somatic cell, the complete genome of the cell undergoing cell division is replicated. This involves large scale DNA synthesis by the cell and enables both daughter cells to receive identical copies of the genetic material. When $^3$H-thymidine is included in the culture media of cells which are synthesizing DNA in preparation for cell division then the labeled thymidine is incorporated into the newly synthesized DNA. The extent of incorporation of $^3$H-thymidine into a population of cells is proportional to the rate of DNA synthesis. by this population of cells and therefore an indication of their cellular proliferation.

The following test was employed to determine whether organic chick pea extracts have phytoestrogenic activity -and whether this activity is equivalent to at least 1 nM estradiol:

ZR75 cell line is a ductal breast carcinoma cell line, originally isolated from malignant mammary epithelium of a sixty-three year old Caucasian female (Engel et al., Human breast carcinoma cells in continuous culture: A review., Cancer Res., 38: 4327–4339, 1978) This cell line contains receptors for estrogen, progesterone and other steroid hormones, but responds through an increase in proliferation only to estrogen. The cell line contains high affinity estrogen-specific receptors. Therefore, this cell line is used for testing estrogen-like activity (Markiewicz et al., In vitro bioassays of non-steroidal phytoestrogens, J. Steroid Biochem. Molec. Biol., 45: 399–405, 1993).

1. ZR75 cells (from American Type Culture Collection, Rockville, Md.) were grown in RPMT1640 media (from Gibco Life Technologies) with 10% fetal bovine serum (FBS), 100 units penicillin per ml and 100 units of streptomycin per ml. The media did not contain Phenol Red (a weak estogen mimetic). The. cells were seeded at a density of one million per 75 cm2 flask. For the experiment, the cells were seeded in 24 well plates at 100,000 cells per ml per well.
2. After growing for 24 hours, the media was removed, the cells were washed with PBS and 1 ml of RPMI 1640 without serum (but with streptomycin and penicillin) was added. Stock solutions of chick pea extract in dimethyl sulfoxide. (DMSO) and estradiol in water were prepared. Various concentrations of organic chick pea extract and estradiol, as indicated in Table 1, were then dosed directly into each well. After another 24 hours, one loci of [methyl-3H] thymidine was added to each well. The media was removed after 24 hours. The cells were washed once in PBS, the PBS was removed completely and the cells were left on ice to incubate with 1 ml per well of10% TCA (trichlioroacetic acid) for 30 minutes. The plates were washed 3 times with 5% TCA to remove all traces of thymidine which wasn't incorporated into the cells. 500 μl of 0.1M sodium hydroxide was added to each well and the plates were incubated at room temperature for at least 30 minutes. 250 μl of each sample was transferred to scintillation vials and after adding 5 ml of counting fluid, the vials were counted for 5 minutes each on a setting for tritium. Data from triplicate wells were calculated as % thymidine incorporation into DNA compared to that of control wells which did not receive any chick pea extract or estradiol. Values were expressed as mean of triplicate wells ± standard deviation.

The results that were obtained are summarized in Table 1.

TABLE 1

| Estradiol (nM) | ZR 75 DNA synthesis (% of Control) | Chick pea DCM extract ($\mu$g/ml) | ZR 75 cell DNA synthesis (% of Control) |
|---|---|---|---|
| 0 | 100 ± 10 | 0 | 100 ± 17.5 |
| 0.01 | 117 ± 19.7 | 0.01 | 106 ± 12.8 |
| 0.1 | 106 ± 16.3 | 0.1 | 176 ± 25.6* |
| 1.0 | 162 ± 3.2* | 1.0 | 174 ± 16.6* |
| 10.0 | 267 ± 15.1* | 10.0 | 226 ± 28.7* |
| 100 | 203 ± 51.2* | | |
| 1000 | 178 ± 20.1* | | |

*indicates statistically significant stimulation of DNA synthesis compared to control at p level < 0.05.

As can be seen from the results in Table 1, 1 nM (0.274 ng/ml) or higher concentrations of estradiol increased DNA synthesis of ZR75 cells. Similar activity of this particular extract of chick peas was obtained at a concentration of 0.1 $\mu$g/ml or higher.

The organic chick pea extract is suitable for use in the inventive compositions in an amount such as to deliver estrogenic activity equivalent to at least 1 nM of estradiol. For this particular extract, concentration of 0.1 $\mu$g of chick peas per 1 ml of media delivered the requisite activity.

EXAMPLE 2

Example 1 was repeated twice with various concentrations of chick pea extract as indicated in Table 2.

The results that were obtained are summarized in Table 2.

TABLE 2

| Treatment | cpm ± SD | % of Control | p value |
|---|---|---|---|
| Experiment 2: | | | |
| Control | 14566 ± 719 | 100 ± 4.9 | |
| Estradiol (10 nM) | 122254 ± 3940 | 839 ± 27 | 0.000003 |
| Chick pea DCM extract (10 $\mu$g/ml) | 22530 ± 1302 | 154.6 ± 8.9 | 0.0016 |
| Experiment 3: | | | |
| Control | 14302 ± 1669 | 100 ± 11.6 | |
| Estradiol (10 nM) | 30158 ± 1087 | 211 ± 7.6 | 0.0004 |
| Chick Pea DCM extract (1.0 $\mu$g/ml) | 26053 ± 901 | 182 ± 6.3 | 0.0009 |
| Chick Pea DCM extract (10.0 $\mu$g/ml) | 49541 ± 591 | 346 ± 2.1 | 0.000005 |

It can be seen from the results in Table 1 (representing Experiment 1) and Table 2 that in 3 separate experiments performed on 3 separate days using 3 different passages of the ZR75 cells, the organic chick pea extract stimulated ZR75 cell proliferation significantly.

EXAMPLE 3

This example illustrates that keratinocytes treated with an organic chick pea extract excreted a substance which stimulated the proliferation of fibroblasts.

Cell Culture of Keratinocytes:

Human keratinocytes, isolated from neonatal foreskin by trypsin treatment were grown in Dulbecco Modification Eagle (DME) Hams F12 (3:1) medium/5% fetal calf serum in the presence of mitomycin C treated 3T3 mouse fibroblasts for establishing dividing keratinocyte colonies. Cells were grown under the above condition until their second passage and kept frozen for future use. Frozen second passage keratinocytes were thawed and plated into the above medium and grown for five days. On day 5, when the cells were 70–80% confluent, they were trypsinized and plated at 20,000–30,000 cells per well in 24 well plates in a serum free keratinocyte growth medium (KGX-from Clonetics, San Diego Calif.) containing 0.15 mM calcium. The cells were grown to 80% confluence for 5 days before the experiment.

Cell Culture of Fibroblasts:

Neonatal human foreskin fibroblasts obtained from Clonetics Corporation (San Diego, Calif.) were cultured in DMEM containing 10% fetal bovine serum (both obtained from Life Technologies, Grand Island, N.Y.). The experiments were carried out in cells in their 5 to 15th passage. Cells were plated at 7,000–10,000 cells per well in 24-well plates and grown to 80% confluence for 5 days. before the experiment.

Preparation of Keratinocyte Conditioned Medium:

For experiments looking for the interaction of keratinocytes and fibroblasts in response to treatment with chick pea extracts, keratinocyte conditioned medium was prepared as follows: 80% confluent keratinocytes prepared as described before, were treated with various concentrations of chick pea extracts (as indicated at Table 3) for 24 hrs in RPMI medium without serum and phenol red. The medium collected from the plates is referred to as "keratnocyte conditioned medium.

Test Methodology:

Keratinocytes and fibroblasts were separately dosed with various concentrations of the chick pea extract in 1 ml of RPMI medium without serum and phenol red. Fibroblasts were also dosed with 1 ml of keratinocyte conditioned medium. After 24 hours, $^3$H thymidine was added at 1 $\mu$Ci per well and the cells were incubated for 24 hrs. Amount of $^3$H thymidine associated with the cellular DNA were assessed as described in step 2 of Example 1.

The results that were obtained are summarized in Table 3.

TABLE 3

| Treatment | Keratinocytes cpm ± SD (% of control) | Fibroblasts cpm ± SD (% of control) | Keratinocyte conditioned medium on fibroblasts cpm ± SD (% of control) |
|---|---|---|---|
| Control | 105514 ± 19070 (100 ± 18.1) | 32206 ± 1207 (100 ± 3.7) | 24385 ± 3056 (100 ± 12.5) |
| Chick Pea DCM extract: | | | |
| 0.1 $\mu$g/ml | 109855 ± 28739 (104 ± 27.2) p = 0.838 | 39617 ± 6046 (123 ± 18.7) p = 0.1057 | 47799 ± 3920 (196 ± 16.0) p = 0.00132 |
| 1.0 $\mu$g/ml | 105596 ± 19888 (100 ± 18.8) p = 0.996 | 35237 ± 3279 (109 ± 10.2) p = 0.2074 | 42093 ± 5448 (172 ± 1.83) p = .0079 |

The results in Table 3 demonstrate that chick pea extracts F did not have a direct effect on either keratinocyte or fibroblast proliferation. However, the chick pea extract induced keratinocytes to secrete growth promoting substances for fibroblasts since conditioned medium from keratinocytes exposed to chick pea extract significantly increased the proliferation of fibroblasts.

EXAMPLE 4

This example illustrates that organic chick pea extracts increase proliferation of cells in the epidermal portion of the piglet skin. In this example, estradiol, pure phytoestrogenic compounds, and chick pea extracts were tested for their effects on epidermal cell proliferation.

Piglet Skin Organ culture:

Pig skin is morphologically and biochemically similar to human skin and is therefore used commonly for testing the effects of materials for, human topical use. Fresh shaved skin from piglets was obtained from the local slaughter house, washed with Dove® Soap and dermatomed at 200µ thickness to obtain the top epidermis and dermal layer. Uniform punch biopsies of the dermatomed pig skin was taken using a 7 mm punch. The biopsies were washed in medium containing high antibiotic/antimycotic mix(Kanamycin and penicillin and streptomycin from Gibco) and incubated for 3 days in high glucose DMEM medium containing hydrocortisone, L-glutamine, antibiotic and antimycotic in the absence of serum in transwell plates, 3 biopsies per well. The medium was fed from the bottom of the transwell so that the epidermal side of the biopsies was in contact with air. On the 3rd day, the medium was changed to fresh medium, and the biopsies were exposed to the various concentrations of various actives in 1 µl of DMSO, as indicated in Table 4. 3 days later, medium was changed, actives readded and the biopsies were labeled with 10 µCi of 3H thymidine per well. After washing the biopsies in PBS, the epidermis was split from the dermis by incubating the biopsies for 24 hrs in 2 M sodium bromide solution with shaking. The epidermis was peeled off from the dermis using a tweezer and dissolved in1 ml of 0.5N NaOH with overnight incubation at 60 ° C. 200 µl of the dissolved epidermis was used for scintillation counting to determine the amount of $^3$H thymidine incorporation into the epidermis. The data was calculated as mean cpm for at least 4 replicates, and was also calculated as % of control biopsies which received no actives. The results that were obtained are summarized in Table 4.

TABLE 4

| Treatment | cpm ± SD | % of Control | p value |
|---|---|---|---|
| Experiment 1 | | | |
| Control | 4563 ± 1523 | 100 ± 33.3 | |
| Estradiol | | | |
| 1 nM | 2690 ± 1113 | 58.9 ± 24.4 | |
| 10 nM | 5190 ± 1096 | 113 ± 24 | 0.476 |
| 100 nM | 1757 ± 1492 | 39.0 ± 32.6 | |
| Isoflavonoids | | | |
| Control | 3789 ± 1164 | 100 ± 30.7 | |
| Daidzein 1 µg/ml | 8599 ± 927 | 227 ± 24.4 | 0.000226 |
| 10 µg/ml | 11065 ± 2901 | 292 ± 76.5 | 0.00228 |
| Formononetin 1 µg/ml | 4770 ± 1260 | 126 ± 33.2 | 0.826 |
| 10 µg/ml | 6608 ± 2886 | 174 ± 76.1 | 0.1867 |
| Chick Pea DCM extract | | | |
| 0.1 µg/ml | 10922 ± 3887 | 288 ± 102 | 0.0099 |
| 1.0 µg/ml | 13149 ± 3037 | 347 ± 80 | 0.000686 |
| Experiment 2 | | | |
| Control | 1155 ± 69 | 100 ± 5.9 | |
| Estradiol 1 nM | 2273 ± 783 | 196 ± 67.7 | 0.1147 |
| Estradiol 10 nM | 3817 ± 1175 | 330 ± 101 | 0.0292 |
| Estradiol 100 nM | 2785 ± 751 | 241 ± 65 | 0.0339 |
| Chick Pea Methanol extract | | | |
| Control | 4451 ± 1961 | 100 ± 44 | |
| 0.01 µg/ml | 5503 ± 3026 | 123 ± 67.9 | 0.5463 |
| 0.1 µg/ml | 8435 ± 2034 | 189 ± 45.6 | 0.0205 |
| 1 µg/ml | 2256 ± 704 | 50.6 ± 15.8 | — |

It can be seen from the results in Table 4 that in 2 separate experiments, estradiol at 10 nM increased proliferation of the piglet epidermal cells (in experiment 2, the increase was statistically significant) Daidzein also demonstrated this effect, daidzein being more effective than the natural hormone estradiol. Another isoflavone, formononetin had no significant growth stimulating effects on pig epidermis. Both methanolic and dichloromethane extracts of chick pea also had growth promoting effect dichloromethane extract being more effective than methanolic extract. Dichlomethane extract of chick pea was even more effective than the pure isoflavones or estradiol. The results demonstrate the beneficial effects of organic chick pea extract on skin cells in a model system which resembles very closely human skin.

Examples 5–10 illustrate skin care compositions according to the present invention. The" compositions can be processed in conventional manner. They are suitable for cosmetic use. In particular, the compositions are suitable for application to wrinkled, lined, rough, dry, flaky, aged and/or UV-damaged skin to improve the appearance and the feel thereof as well as for application to healthy skin to prevent or retard deterioration thereof.

EXAMPLE 5

This example illustrates a high internal phase water-in-oil emulsion incorporating the inventive composition.

| | % w/w |
|---|---|
| CHICK PEA DCM EXTRACT | 0.5 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 6

This example illustrates an oil-in-water cream incorporating the inventive composition.

| | % w/w |
|---|---|
| CHICK PEA METHANOL EXTRACT | 2 |
| Mineral oil | 4 |
| 1,3-dimethyl-2-imidazolidinone | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10) Alfol 16RD is cetyl alcohol

EXAMPLE 7

This example illustrates an alcoholic lotion incorporating the composition according to the invention.

|                                  | % w/w    |
|----------------------------------|----------|
| CHICK PEA METHANOL EXTRACT       | 5        |
| 1,3-dimethyl-2-imidazolidinone   | 0.1      |
| Ethanol                          | 40       |
| Perfume                          | qs       |
| Butylated hydroxy toluene        | 0.01     |
| Water                            | to 100   |

EXAMPLE 8

This example illustrates another alcoholic lotion containing the inventive composition.

|                                  | % w/w    |
|----------------------------------|----------|
| CHICK PEA DCM EXTRACT            | 10       |
| 1,3-dimethyl-2-imidazolidinone   | 0.01     |
| Ethanol                          | 40       |
| Antioxidant                      | 0.1      |
| Perfume                          | qs       |
| Water                            | to 100   |

EXAMPLE 9

This example illustrates a suncare cream incorporating the composition of the invention:

|                                  | % w/w    |
|----------------------------------|----------|
| CHICK PEA ETHANOL EXTRACT        | 2        |
| 1,3-dimethyl-2-imidazolidinone   | 0.2      |
| Silicone oil 200 cts             | 7.5      |
| Glycerylmonostearate             | 3        |
| Cetosteryl alcohol               | 1.6      |
| Polyoxyethylene-(20)-cetyl alcohol | 1.4    |
| Xanthan gum                      | 0.5      |
| Parsol 1789                      | 1.5      |
| Octyl methoxycinnate (PARSOL MCX)| 7        |
| Perfume                          | qs       |
| Color                            | qs       |
| Water                            | to 100   |

EXAMPLE 10

This example illustrates a non-aqueous skin care composition incorporating the inventive combination.

|                                  | % w/w    |
|----------------------------------|----------|
| CHICK PEA DCM EXTRACT            | 5        |
| 1,3-dimethyl-2-imidazolidinone   | 1        |
| Silicone gum SE-30[1]            | 10       |
| Silicone fluid 345[2]            | 20       |
| Silicone fluid 344[3]            | 50.26    |
| Squalene                         | 10       |
| Linoleic acid                    | 0.01     |
| Cholesterol                      | 0.03     |
| 2-hydroxy-n-octanoic acid        | 0.7      |
| Vitamin E linoleate              | 0.5      |
| Herbal oil                       | 0.5      |
| Ethanol                          | 2        |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the allowing appended claims in determining the full scope of the invention.

What is claimed is:
1. A skin care composition comprising:

(i) an organic extract of chick peas in an amount such as to provide an estrogenic activity equivalent to at least 1 nM of estradiol.

(ii) a cosmetically acceptable vehicle.

* * * * *